US009912917B2

(12) United States Patent
Seesselberg et al.

(10) Patent No.: US 9,912,917 B2
(45) Date of Patent: Mar. 6, 2018

(54) VISUALIZATION APPARATUS FOR A SURGICAL SITE

(71) Applicant: Carl Zeiss Meditec AG, Jena (DE)

(72) Inventors: Markus Seesselberg, Aalen (DE); Joachim Steffen, Westhausen (DE); Steffen Siegler, Aalen (DE); Christian Voigt, Abtsgmuend (DE)

(73) Assignee: Carl Zeiss Meditec AG, Jena (DE)

( * ) Notice: Subject to any disclaimer, the term of this patent is extended or adjusted under 35 U.S.C. 154(b) by 236 days.

(21) Appl. No.: 14/941,468

(22) Filed: Nov. 13, 2015

(65) Prior Publication Data

US 2016/0142683 A1 May 19, 2016

(30) Foreign Application Priority Data

Nov. 13, 2014 (DE) .................... 10 2014 223 181

(51) Int. Cl.
H04N 9/47 (2006.01)
H04N 7/18 (2006.01)
G02B 27/26 (2006.01)
A61B 90/00 (2016.01)
G02B 17/00 (2006.01)
G02B 26/08 (2006.01)
H04N 5/225 (2006.01)
G02B 21/00 (2006.01)
A61B 19/00 (2006.01)

(52) U.S. Cl.
CPC ............ H04N 7/183 (2013.01); A61B 90/36 (2016.02); G02B 17/008 (2013.01); G02B 26/0816 (2013.01); G02B 27/26 (2013.01); H04N 5/2254 (2013.01); A61B 2019/5221 (2013.01); G02B 21/0012 (2013.01)

(58) Field of Classification Search
CPC .. G08B 13/19656; H04N 7/181; H04N 7/183; H04N 7/18; H04N 7/188
USPC .......................................... 348/143
See application file for complete search history.

(56) References Cited

U.S. PATENT DOCUMENTS 594,028 A * 11/1897 Ishikawa ................. B07B 13/00
198/832
5,867,210 A * 2/1999 Rod ....................... G02B 21/22
348/51

* cited by examiner

Primary Examiner — William C Vaughn, Jr.
Assistant Examiner — Daniel Tekle
(74) Attorney, Agent, or Firm — Walter Ottesen, P.A.

(57) ABSTRACT

A visualization apparatus for a surgical site includes a recording unit for recording an image of an object arranged in a focal plane of the recording unit. The recording unit has a lens having an optical axis that intersects the focal plane at a point P. An electronic image representation unit has an image surface for reproducing the recorded image and point P is reproduced at image point P'. A mirror unit has a mirror surface, which has a center point S and is arranged relative to the image surface such that the reproduced image is reflected by the mirror surface. The focal plane, image surface and mirror surface are arranged relative to one another such that an observation point B results for which the following applies:

$-2\,D < \Phi_1 - \Phi_2 < +2\,D;$ wherein:
$\Phi_1 = -1/d_1$
$\Phi_2 = -1/d_2$
$d_1 =$ distance $\overline{PB}$
$d_2 =$ distance $\overline{PS}+$distance $\overline{SB}$.

20 Claims, 11 Drawing Sheets

VISUALIZATION APPARATUS FOR A SURGICAL SITE

CROSS REFERENCE TO RELATED APPLICATION

This application claims priority of German patent application no. 10 2014 223 181.7, filed Nov. 13, 2014, the entire content of which is incorporated herein by reference.

FIELD OF THE INVENTION

The invention relates to a visualization apparatus for a surgical site, including an image recording unit for recording an image of an object arranged in a focal plane of the image recording unit, wherein the image recording unit has a lens having an optical axis that intersects the focal plane at a point P. The visualization apparatus includes an electronic image representation unit having an image representation surface for reproducing the image recorded by the image recording unit, wherein the point P is reproduced at an image point P' by the image representation surface of the image representation unit.

BACKGROUND OF THE INVENTION

Visualization apparatuses are a necessary prerequisite for surgical procedures on very small and fine body structures. Such operations may even involve the participation of two observers or surgeons who, for example in spinal operations, are situated opposite one another in a 180° arrangement.

Traditional visualization apparatuses form surgical microscopes that are typically arranged directly between observer and an operation site. With the use of digital visualization apparatuses, by contrast, the operation site is recorded by an image recording unit and represented in a magnified fashion for each observer on an image representation unit.

U.S. Pat. No. 5,867,210 describes a method for representing images of a stereoscopic surgical microscope with a video camera. The image of the video camera is displayed on a first image representation unit for a first observer and a second image representation unit for a second observer. Both observers have to wear special spectacles in order to be able to view a stereoscopic image.

What is disadvantageous about this method is that a dedicated image representation unit has to be present for each observer. The image representation units occupy a relatively large amount of space and can lead to a restriction of the working space and the freedom of movement of the observer or of the respective other observer. Each change of view between operation site and image representation unit involves a head movement and an accommodation of the eyes of the observer. For observers aged 40 or more, there is an increasing reduction in the elasticity of the eye lens, and the accommodation times increase as a result. A head movement governed by the arrangement of the image representation unit, and the changing accommodation of the eyes that is associated therewith can lead to unergonomic work. The consequence is more rapid fatigue of the observer.

For observers with presbyopia, it is possible that either the operation site or the image representation unit no longer lies in the accommodation range of the observer, such that the observer requires further aids such as varifocal spectacles, for example, in order to be able to accommodate to the operation site and the image representation unit. However, the use of varifocal spectacles is disadvantageous because objects at a specific distance can be observed well thereby only at a specific viewing angle.

SUMMARY OF THE INVENTION

It is an object of the invention to provide a visualization apparatus for a surgical site which enables ergonomic and fatigue-free work.

According to the invention, a visualization apparatus includes a first mirror unit having a first mirror surface, which has a first center point S and which is arranged relative to the image representation surface in such a way that the image reproduced by the image representation surface is reflected by the first mirror surface. The focal plane, the image representation surface and the first mirror surface are arranged relative to one another in such a way that a first observation point B results, for which it holds true that:

$-2$ D$<\Phi 1-\Phi 2<+2$ D, preferably $-1$ D$<\Phi 1-\Phi 2<+1$ D, particularly preferably $-0.5$ D$<\Phi 1-\Phi 2<+0.5$ D; wherein the following applies:

$\Phi 1 = -1/d_1$
$\Phi 2 = -1/d_2$
$d_1 =$ distance $\overline{PB}$
$d_2 =$ distance $\overline{P'S}$ + distance $\overline{SB}$ A surgical site is recorded by an image recording unit having a lens having an optical axis. An object to be observed at the operation site in this case lies in the focal plane of the image recording unit. The optical axis of the lens intersects the focal plane at a point P. The image recorded by the image recording unit with the point P is displayed, for example in a magnified fashion, by an electronic image representation unit. An image representation surface of the image representation unit shows an imaging of the focal plane with an image point P'. The image point P' has the image information of the point P. A beam leads from the image representation surface with the image point P', in a manner deflected by a first mirror surface of a first mirror unit, to a first observation point B.

The first observation point B is the point that an observer can occupy in order to be able to alternately view the operation site with the point P and the mirror surface that mirrors the image of the image representation surface with the image point P'. In this case, the viewing direction is changed merely by means of a slight movement of the eyes, without a movement of the head.

In a first viewing direction, the observer can directly view the operation site with the point P. A distance $d_1 = \overline{PB}$ is the distance between the point P and the first observation point B. The observer's eye is thus set to the distance $d_1$. The unit of the distance $d_1$ is meters. The distance $d_1$ corresponds to a first accommodation distance. The eye then has the accommodation $\Phi 1 = -1/d_1$. The unit of the accommodation $\Phi 1$ is D (diopters).

In a second viewing direction, the observer can view the image of the image representation surface with the image point P' on the first mirror surface, wherein the image of the image representation surface is deflected via the mirror surface. The image point P' on the image representation surface is reflected at the first mirror surface at a first center point S. A distance $d_2 = \overline{P'S} + \overline{SB}$ is the sum of the two distances between the image point P' and the first center point S and between the first center point S and the first observation point B. The first center point S is defined for example by the area centroid of the first mirror surface. In this second viewing direction, the observer's eye is set to the distance $d_2$. The unit of the distance $d_2$ is meters. The distance $d_2$ corresponds to a second accommodation distance. The eye then has the accommodation $\Phi 2=-1/d_2$. The unit of the accommodation $\Phi 2$ is D (diopters).

In the ideal state, the distance $d_1$ and the distance $d_2$ are of identical magnitude and hence the difference $\Phi 1-\Phi 2=0$. In practice, a slight deviation from this ideal state is still acceptable. According to the invention, the difference $\Phi 1-\Phi 2$ is in a range of between $-2$ D and $+2$ D, preferably between $-1$ D and $+1$ D, particularly preferably between $-0.5$ D and $+0.5$ D.

During a surgical procedure, the viewing direction of the observer is directed at the operation site. The mirror surface is arranged in the observer's field of view in such a way that the observer can change the view between operation site and mirror surface merely by changing the viewing direction and without needing to move his/her head, since working direction and viewing direction are approximately identical. An approximately identical accommodation distance between "eye and operation site" (distance $d_1$) and between "eye and image representation unit via the first mirror surface" (distance $d_2$) is thus provided for the eye of the first observer. This has the advantage for the observer that ergonomically expedient and fatigue-free work is made possible in conjunction with little or constant accommodation when changing view between operation site and mirror surface. As a result, longer operation times are possible, particularly for presbyopic observers or surgeons. The case can occur that for a presbyopic observer, without a further visual aid, the possibility of performing an operation actually exists in the first place by virtue of the apparatus according to the invention.

The deflection of the image of the image representation unit via the first mirror surface makes it possible for the image representation unit to be arranged outside the surgeon's field of view, for example directly below the ceiling of the room. The advantage is a space-saving arrangement of the image representation unit in the usually confined operation area.

The first mirror unit having the first mirror surface can be made smaller and lighter than the image representation unit. For a small and light mirror unit, a mechanical mount can be realized in a lightweight configuration with little mechanical outlay; consequently, the observer's working space is restricted only slightly.

In principle, the conditions for the observation point B hold true in the same way for the right and left eyes of the observer. In practice, it can also be assumed that the observation point B lies in the center between the two eyes. The conditions for accommodation thus still lie in the specified region.

In one configuration of the invention, the first mirror unit has a device for rotating the first mirror surface about at least one axis and/or a device for changing a distance between the first mirror surface and the focal plane and/or a device for displacing the first mirror surface parallel to the focal plane.

Rotation of the first mirror surface about at least one axis and/or a change in the distance between the first mirror surface and the focal plane enable(s) adaptation to different body sizes in the event of a change of observer. In the event of a change in position of the observer, the mirror surface can be set in terms of angle and/or in terms of distance from the focal plane and/or by a displacement parallel to the focal plane in such a way that the observer can view the image representation unit optimally in the changed position as well. The distance $d_2$ can thereby be set in such a way that the abovementioned condition for the difference $\Phi 1-\Phi 2$ is fulfilled.

In one configuration of the invention, a second mirror unit having a second mirror surface is present, which has a second center point S' and which is arranged relative to the image representation surface in such a way that the image reproduced by the image representation surface is reflected by the second mirror surface, wherein the focal plane, the image representation surface and the second mirror surface are arranged relative to one another in such a way that a second observation point B' results, for which it holds true that:

$-2$ D$<\Phi 3-\Phi 4<+2$ D, preferably $-1$ D$<\Phi 3-\Phi 4<+1$ D, particularly preferably $-0.5$ D$<\Phi 3-\Phi 4<+0.5$ D; wherein the following applies:

$\Phi 3=-1/d_3$
$\Phi 4=-1/d_4$
$d_3=$distance $\overline{PB'}$
$d_4=$distance $\overline{P'S'}+$distance $\overline{S'B'}$ A second observer can view the imaging of a point P of the focal plane as a point P' on the image representation surface via a second mirror surface. A second observation point B' is the point that can be occupied by the second observer in order to observe both the operation site with the point P and the, for example magnified, image of the operation site with the image point P' as displayed by the image representation surface. The image point P' on the image representation surface is mirrored at the second mirror surface at a second center point S'. The unit of the accommodation $\Phi 3$ and $\Phi 4$ is D (diopters). The same advantages already described above for the first observer hold true for the second observer.

The first mirror surface and the second mirror surface are arranged in such a way that they deflect the light rays coming from image representation units such that an observer at the observation point B or B' can perceive the information represented by the image representation surface. Advantageously, only a single image representation unit having an image representation surface is necessary for both observers. Merely by adding the second mirror unit having the second mirror surface it is possible to extend the visualization apparatus cost-effectively for a second observer, without restricting the working space of the first observer. What is crucial here is that both observers can view a laterally correct image of the image representation unit with correct depth relation. For both observers, ergonomic and fatigue-free work is possible in conjunction with little or constant accommodation when changing view between operation site and mirror surface.

In one configuration of the invention, the second mirror unit has a device for rotating the second mirror surface about at least one axis and/or a device for changing a distance between the second mirror surface and the focal plane and/or a device for displacing the second mirror surface parallel to the focal plane.

The setting possibility for the second mirror unit enables individual adaptation to the body size and/or position of a second observer. The distance $d_4$ can be set by an adaptation of the distance between the second mirror surface and the focal plane in such a way that the abovementioned condition for the difference $\Phi 3-\Phi 4$ is fulfilled.

In one configuration of the invention, the image representation unit is arranged above the image recording unit.

In the case of this arrangement, the image representation unit can be arranged in a space-saving manner in a region which does not lie in the working region of the observer.

In one configuration of the invention, the image representation surface is aligned at an angle of a maximum of 15° parallel to the focal plane, wherein an emission direction of the image representation surface is directed to the focal plane.

In this arrangement, the image representation unit can be fitted in a space-saving manner, for example in the region below a ceiling of the room. Consequently, the image representation unit is not situated in the working region of the observer or in the field of view of the operation site. If the emission direction of the image representation surface is implemented in the direction of the focal plane downward, the first mirror surface and/or the second mirror surface can be arranged ergonomically expediently.

In one configuration of the invention, the image representation surface is arranged in such a way that a center point of the image representation surface lies in the extension of the optical axis of the lens of the image recording unit.

This arrangement results in simple geometrical relationships in the arrangement of the image recording unit, the image representation surface, and the first mirror surface and/or the second mirror surface. The image representation unit having the image representation surface can be connected to the operating table or the image recording unit via a mount. An arrangement of the image representation unit in this position can bring about an expedient center-of-gravity situation. An expedient center-of-gravity situation can positively influence the damping behavior in the case of possible vibrations of the mount.

In one configuration of the invention, the first mirror surface and/or the second mirror surface are/is arranged in each case between the image recording unit and the image representation surface.

If the first mirror surface and/or the second mirror surface are/is arranged between the image recording unit and the image representation surface, this means that the first center point S and/or the second center point S' are/is in each case at a distance of a maximum of 0.5 meter perpendicularly to the connecting line between the point P and the image point P'. In this configuration, the first mirror surface and/or the second mirror surface can be arranged in an ergonomically expedient position. The overall system including image recording unit, image representation unit and the first and/or second mirror surface can be fashioned ergonomically expediently and in a space-saving manner in the usually confined operation area.

In one configuration of the invention, the image recording unit is configured for recording a stereoscopic image and the image representation surface is configured for reproducing the stereoscopic image.

A stereoscopic image recording unit enables the recording of the operation site from two viewing angles. Advantageously, spatial and depth information can be acquired optically more easily. A stereoscopic image representation surface enables the reproduction of a stereoscopic image recorded by a stereoscopic image recording unit and thus enables a better spatial and depth perception of the operation site for the observer.

In one configuration of the invention, a $\lambda/2$ retardation plate is arranged in the beam path between the image representation surface and the first mirror surface or in the beam path between the image representation surface and the second mirror surface.

In the case of stereoscopic image reproduction, the separation of the two image channels for the right and left eyes can be effected via differently polarized light. For this purpose, linearly polarized light can be used, such that each stereoscopic partial image is coded with light rays having mutually perpendicular directions of polarization. Alternatively, however, the two partial images can also be coded with light rays that are right-circularly and respectively left-circularly polarized. In both cases, with two mirror surfaces arranged opposite, for example, two observers have to wear different polarization spectacles in order to obtain a correct depth impression. Since both observers wear different polarization spectacles in this case, the first stereoscopic partial image appears in the right eye of a first observer and in the left eye of a second observer. The introduction of a $\lambda/2$ retardation plate into one of the two beam paths brings about an inversion of the direction of polarization for this beam path. For two observers arranged opposite, this has the advantage that both observers can wear identical polarization spectacles. In the event of the observation positions being changed, it is not necessary to change the polarization spectacles.

In one configuration of the invention, the first mirror surface or the second mirror surface has a $\lambda/4$ retardation layer.

If the first mirror surface or the second mirror surface has a $\lambda/4$ retardation layer, this brings about an inversion of the direction of polarization for this beam path, in a manner similar to that when introducing a $\lambda/2$ retardation plate. The $\lambda/4$ retardation layer can be applied to a mirror surface in a space-saving manner, thereby obviating the introduction of an additional component into a beam path. If two observers change an opposite observation position, it is not necessary to change the polarization spectacles.

In one configuration of the invention, the image representation unit is configured as an autostereoscopic 3D monitor.

In the case of image reproduction with an autostereoscopic 3D monitor, an observer can view the image representation surface without 3D spectacles, in particular without polarization spectacles. This is advantageous when there is a change of view directly to the operation site. The observer can see the operation site without polarization spectacles, which can then be perceived as disturbing. The observation position can be changed at any time.

In one configuration of the invention, the visualization apparatus includes a first actuator, for rotating the first mirror surface about a first axis, and/or a second actuator, for changing the first distance between the first mirror surface and the focal plane. The visualization apparatus includes a first position detection system, for detecting a position of the eyes and/or the head of a first observer relative to the first mirror surface. A control unit is connected to the first position detection system and to the first actuator and/or the second actuator. The control unit is configured in such a way that the rotation of the first mirror surface and/or the change in the distance between the first mirror surface and the focal plane can be set by the position of the eyes and/or the head of the first observer as detected by the first position detection system.

This embodiment has the advantage that, in the event of a change in position of the eyes and/or the head of an observer, the first mirror surface is automatically readjustable with regard to setting angle and/or distance with respect to the focal plane. The observer can view an optimum imaging of the image representation unit at any time. The control can be configured in such a way that the setting angle is readjusted only if the first observer has directed his/her eyes at the first mirror surface.

In one configuration of the invention, the visualization apparatus includes a third actuator, for rotating the second mirror surface about a second axis, and/or a fourth actuator, for changing the second distance between the second mirror surface and the focal plane. The visualization apparatus includes a second position detection system, for detecting a position of the eyes and/or the head of a second observer relative to the second mirror surface. The control unit is connected to the second position detection system and to the third actuator and/or the fourth actuator. The control unit is configured in such a way that the rotation of the second mirror surface and/or the change in the distance between the second mirror surface and the focal plane can be set depending on the position of the eyes and/or the head of the second observer as detected by the second position detection system.

The same advantages in the case of the tracking of the first mirror surface for the first observer also hold true in the case of the tracking of the second mirror surface for the second observer.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
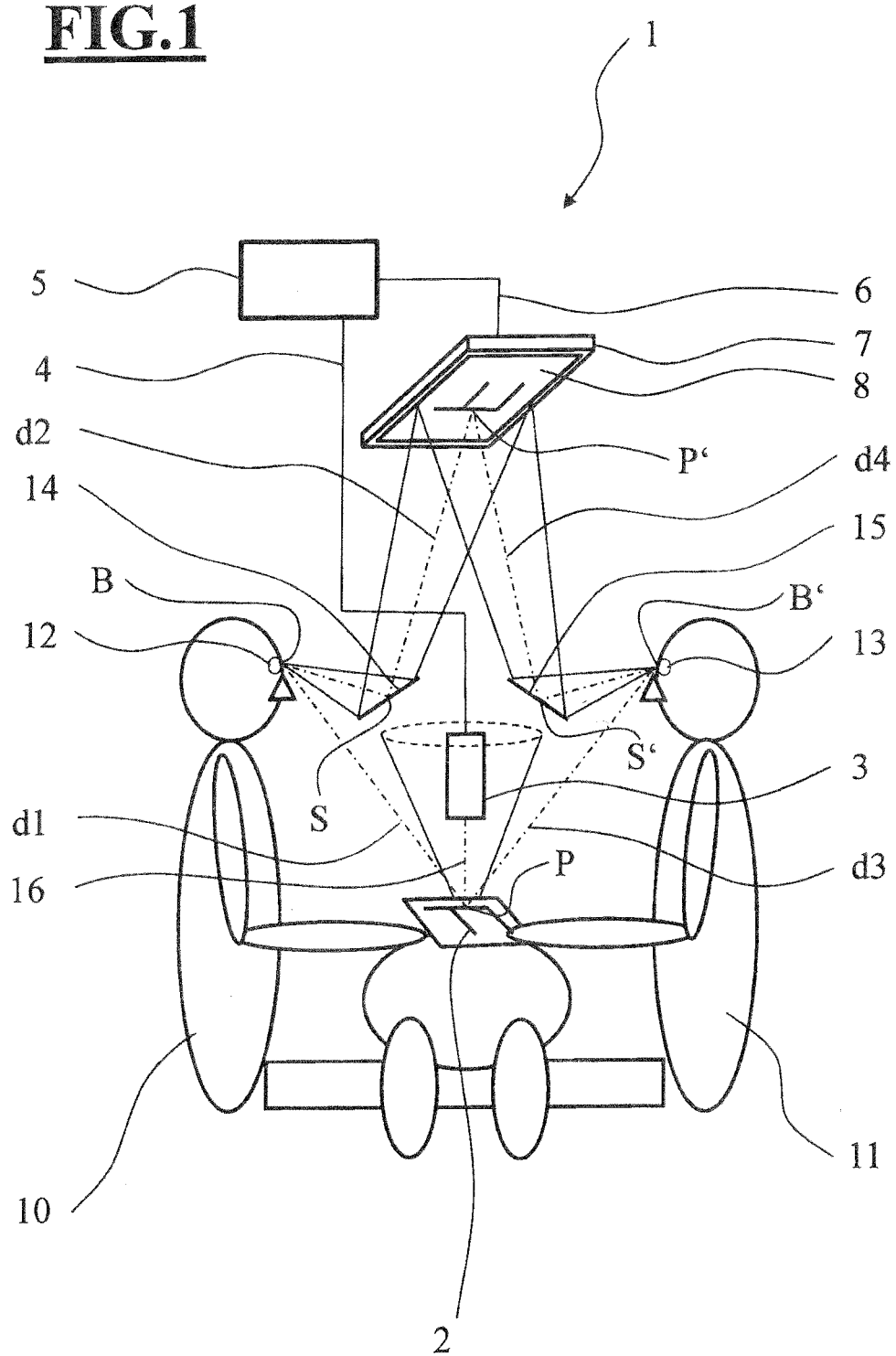
FIG. 1 is a schematic of a surgical site with a first embodiment of a visualization apparatus according to the invention.

FIG. 1 is a schematic illustration of a surgical site with a first embodiment of a visualization apparatus 1 according to the invention.

In a surgical scene, for example a spinal operation, a first observer 10, the main surgeon, and a second observer 11, an assistant, are situated opposite one another.

The surgical site, that is, the region to be operated on, includes a focal plane 2 with a point P. The operation site with the point P is recorded by an image recording unit 3. The image recording unit has an imaging optical unit (not illustrated) having a lens and an optical axis 16 and an image sensor (not illustrated). The image recording unit 3 is connected to a control unit 5 via a first line 4. The control unit 5 is connected to an image representation unit 7 via a second line 6. The control unit 5 can be connected to an input/output unit (not illustrated), for example a graphical user interface.

The image representation unit 7 is arranged above the surgical site and is thus situated in a region which does not lie in a direct or ergonomically expedient viewing direction for the two observers (10, 11). The image representation unit 7 can be arranged below the ceiling of the operating room and an image representation surface 8 of the image representation unit 7 can be aligned in such a way that it is aligned parallel to the focal plane 2.

The image representation unit 7 shows a magnified image of the operation site with the focal plane 2 and the point P on the image representation surface 8. The image of the image representation surface 8 is guided via a first mirror surface 14 to the first observer 10. The first observer 10 can thus view the image of the image representation surface 8 when looking at the mirror surface 14. The second observer 11 sees the image of the image representation surface via a second mirror surface 15. The point P lying in the focal plane 2 is represented by an image point P' on the image representation surface 8 of the image representation unit 7. The image point P' is guided via the first mirror surface 14, in a manner mirrored at a first center point S, to a first eye 12 of the first observer 10. The image of the image point P' is also guided via the second mirror surface 15, in a manner mirrored at a second center point S', to a second eye 13 of the second observer 11.

In this case, the first observer 10 can optionally directly view the operation site with the focal plane 2 or view, via the mirror surface 14, the image of the operation site represented in a magnified fashion by the image representation unit 7. The first observer 10 need not move his/her head for this purpose. The first observer 10 can change between operation site and magnified image merely by slightly changing the viewing direction.

In this case, in the first eye 12 of the first observer 10, a first observation point B results, for which it holds true that:

$$-2\ D < \Phi 1 - \Phi 2 < +2\ D, \text{ preferably } -1\ D < \Phi 1 - \Phi 2 < +1\ D, \text{ particularly preferably } -0.5\ D < \Phi 1 - \Phi 2 < +0.5\ D; \text{ wherein the following applies:}$$

$\Phi 1 = -1/d_1$
$\Phi 2 = -1/d_2$
$d_1 = $ distance $\overline{PB}$
$d_2 = $ distance $\overline{P'S} + $ distance $\overline{SB}$ In a first viewing direction, the first observer 10 can directly view the surgical site with the point P. A distance $d_1 = \overline{PB}$ is a distance between the point P and the first observation point B. The first eye 12 of the first observer 10 is set, in this first viewing direction, to the distance $d_1$ corresponding to a first accommodation distance.

In a second viewing direction, the first observer 10 can view the image of the image representation surface 8 with the image point P' on the first mirror surface 14, wherein the image of the image representation surface 8 is deflected via the mirror surface 14. A distance $d_2 = \overline{P'S} + \overline{SB}$ is the sum of the two distances between the image point P' and the first center point S and between the first center point S and the first observation point B. In this second viewing direction, the first eye 12 of the first observer 10 is set to the distance $d_2$. The distance $d_2$ corresponds to a second accommodation distance.

The distance $d_1$ can be 0.75 meter, for example. The distance $d_2$ is likewise 0.75 meter in the case of optimum arrangement. The distance $\overline{PS}$ is 0.3 meter in this example and the distance $\overline{SB}$ has an absolute value of 0.45 meter. The distance $d_2$ is between 0.375 meter and 1.05 meters, preferably in the range of between 0.525 meter and 0.91 meter, particularly preferably in the range of between 0.675 meter and 0.825 meter. The image representation surface 8 can have an image diagonal of 0.8 meter. The viewing angle, that is, the relative opening region of the field of view, of the first observer 10 is then approximately 30° in the vertical direction and approximately 53° in the horizontal direction. These indications are merely by way of example. The invention also encompasses other distances and size relationships for which the stated conditions are fulfilled.

When looking at the surgical site, the first eye 12 of the first observer 10 has the accommodation $\Phi 1=-1/d_1$. When viewing the second mirror surface, the first eye 12 has the accommodation $\Phi 2=-1/d_2$. In the ideal state, the distance $d_1$ and the distance $d_2$ are of identical magnitude and hence the difference $\Phi 1-\Phi 2=0$. In practice, a slight deviation from this ideal state is still acceptable. According to the invention, the difference $\Phi 1-\Phi 2$ is in a range of between −2 D and +2 D, preferably between −1 D and +1 D, particularly preferably between −0.5 D and +0.5 D. This has the advantage for the observer that fatigue-free and ergonomically expedient work is possible as a result of constant accommodation when changing view between the operation site and the first mirror surface 14.

A similar situation results for the second observer 11. Merely by slightly changing the viewing direction, the second observer 11 can change between direct viewing of the operation site and the magnified representation of the operation site via the second mirror surface 15. In this case, in the second eye 13 of the second observer 11, a second observation point B' results, for which it holds true that:

−2 D<$\Phi 3-\Phi 4$<+2 D, preferably −1 D<$\Phi 3-\Phi 4$<+1 D, particularly preferably −0.5 D<$\Phi 3-\Phi 4$<+0.5 D; wherein the following applies:

$\Phi 3=-1/d_3$
$\Phi 4=-1/d_4$
$d_3$=distance $\overline{PB'}$
$d_4$=distance $\overline{P'S'}$+distance $\overline{S'B'}$ A distance $d_3=\overline{PB'}$ is the distance between the point P and the second observation point B'. A distance $d_4=\overline{P'S'}+\overline{S'B'}$ is the sum of the two distances between the point P' and the second center point S' and between the second center point S' and the second observation point B'.

When looking at the surgical site, the second eye 13 has the accommodation $\Phi 3=-1/d_3$. When viewing the second mirror surface, the second eye 13 has the accommodation $\Phi 4=-1/d_4$. In the ideal state, the distance $d_3$ and the distance $d_4$ are of identical magnitude and hence the difference $\Phi 3-\Phi 4=0$. In practice, a slight deviation from this ideal state is still acceptable. According to the invention, the difference $\Phi 3-\Phi 4$ is in a range of between −2 D and +2 D, preferably between −1 D and +1 D, particularly preferably between −0.5 D and +0.5 D.

The distance $d_1$, distance $d_2$, distance $d_3$ and distance $d_4$ shown in FIG. 1 are illustrated in each case for an individual eye (12, 13) for the two observers (10, 11). The relationships described correspondingly hold true, of course, for the left and right eyes of the two observers (10, 11).

The image representation unit 7 shows a magnified image—mirrored at a vertical plane—of the operation site with the focal plane 2. As a result, the first observer 10 sees a laterally correct, magnified image of the operation site with the focal plane 2 via the first mirror surface 14. The second observer 11 views the focal plane 2 from an opposite side relative to the first observer 10. Through the second mirror surface 15, the second observer sees the magnified image—mirrored at the vertical plane—of the operation site with the focal plane 2 likewise from the opposite side. Therefore, the second observer 2 also views a laterally correct and magnified image of the operation site with the focal plane 2 via the second mirror surface 15.

In principle, the conditions for the first observation point B and the second observation point B' hold true in the same way in each case for the eye pupil of the right and left eyes of the first observer 10 and of the second observer 11. In practice, it can also be assumed that the first observation point B and the second observation point B' lie in each case in the center between the two eyes. The deviations associated therewith are very small and the conditions for accommodation are thus still in the specified range.

The image recording unit 3 can be configured as a monoscopic or stereoscopic camera. The camera includes an image recording chip, for example a CCD chip, and can have further optical elements (not illustrated) for zoom setting and focusing. The image recording unit 3 can also include diaphragms and filter elements. Preferably, the image recording unit is embodied as an HD camera. In addition to the image recording unit 3, an illumination unit (not illustrated) can be arranged in such a way that the focal plane 2 is illuminated by the illumination unit. One example of a stereoscopic camera as image recording unit 3 is a so-called light field camera.

The control unit 5 can be a commercially available computer or a controller specifically provided for this device. The control unit 5 includes input/output channels, a memory and a processor. For driving the image representation unit 7, the control unit 5 typically has a graphics card.

The image representation unit 7 can be a flat screen, a plasma screen or an LED screen. The image representation unit 7 is preferably suitable for an HD resolution. The use of a higher UHD resolution, also referred to as "4K" resolution, is also advantageously possible. By virtue of the arrangement of the image representation unit 7 below the ceiling, at a relatively large distance from the operation site, the image representation unit is exposed only to a relatively low risk of contamination by blood or secretions of a patient and can be kept sterile more easily.

Owing to the arrangement of the first mirror surface and second mirror surface as shown in FIG. 1, it is possible for the mirror unit to be made smaller than the image representation unit. For a small and light mirror unit, a mechanical mount can be realized in a lightweight configuration with little mechanical outlay.

It is conceivable for the image representation unit 7, the first mirror surface 14 and the second mirror surface 15 to be mechanically connected by a stand device. This has the advantage that possible vibrations of the image representation unit have no effects on the image of the first mirror surface 14 or of the second mirror surface 15. The image recording unit 3 can likewise be arranged on the stand device. It is also conceivable for the image representation unit 7 to be arranged such that it is displaceable vertically, horizontally or arbitrarily in space, in order to achieve an optimum adaptation of the distance $d_2$ for a first observer 10 and the distance $d_4$ for a second observer 11.

The image recording unit 3 is arranged in the direction of the surface normal of the focal plane 2. However, it is also conceivable for the image recording unit to form an angle of between 0° and 30° relative to the surface normal of the originally defined focal plane 2. In this case, the image of the image recording unit 3 can be computationally corrected by the control unit 5 in such a way that the image representation unit 7 represents an image of the focal plane 2 from which distortion has been eliminated.

Elements of the following embodiments which correspond to elements of the embodiment described with reference to FIG. 1 are designated by the same reference signs as in FIG. 1.

Changes in position of the first observer 10 or of the second observer 11 during the operation can result in deviations of the ideal viewing angle in regard to the first mirror surface 14 or the second mirror surface 15. This can have the consequence that, for example, only a small part of the image representation unit 7 is visible to the first observer 10 and/or second observer 11 in the mirror surface (14, 15). The consequence would be that the observer (10, 11) would have to manually adapt and adjust the mirror position in order to be able to view the entire image of the image representation unit 7 in the mirror surface (14, 15).

Figure 2:
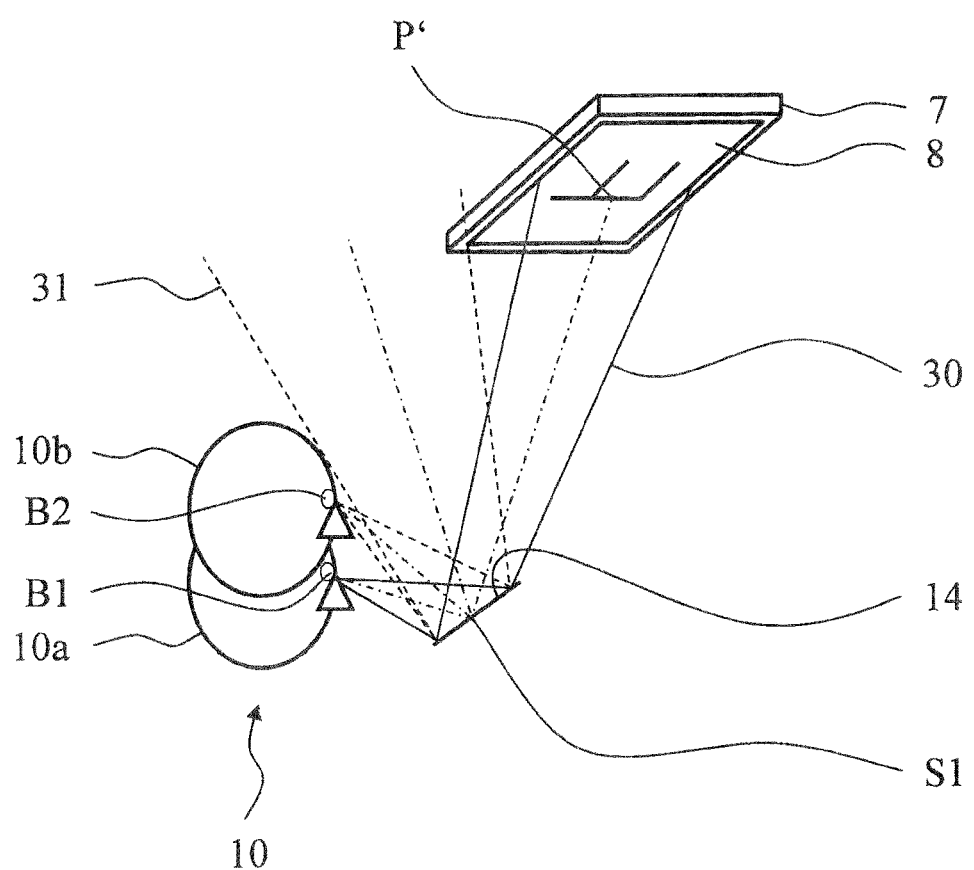
FIG. 2 is a schematic of an observation situation for two different positions of an observer in a side view.

FIG. 2 shows a schematic illustration of an observation situation for two different positions of the first observer 10 in a side view. In a first position 10a, principal rays 30 pass from the eye of the first observer 10 from one point B1 via the first mirror surface 14 to the image representation unit 7. The term principal rays denotes rays which pass from the pupil center of the eye to the screen. FIG. 2 illustrates two principal rays 30 passing from the point B1 to the edge of the image representation surface 8. If the eye of the first observer 10 is situated in the position B1, then the first observer 10 in the first position 10a can view a complete image of the image representation surface 8 in the first mirror surface 14.

A different situation arises if the first observer 10 is situated in a second position 10b. The principal rays change as a result of the position of the head being changed. The principal rays 31 pass from the point B2 via the first mirror surface 14 in the direction of the image representation unit 7. However, the first observer 10 can see only a small part of the image of the image representation surface 8 via the first mirror surface 14 and additionally perceives part of the ceiling structure. The first observer 10 in the second position 10b is thus in an ergonomically unfavorable observation situation and cannot optimally view the image representation surface 8.

Figure 3:
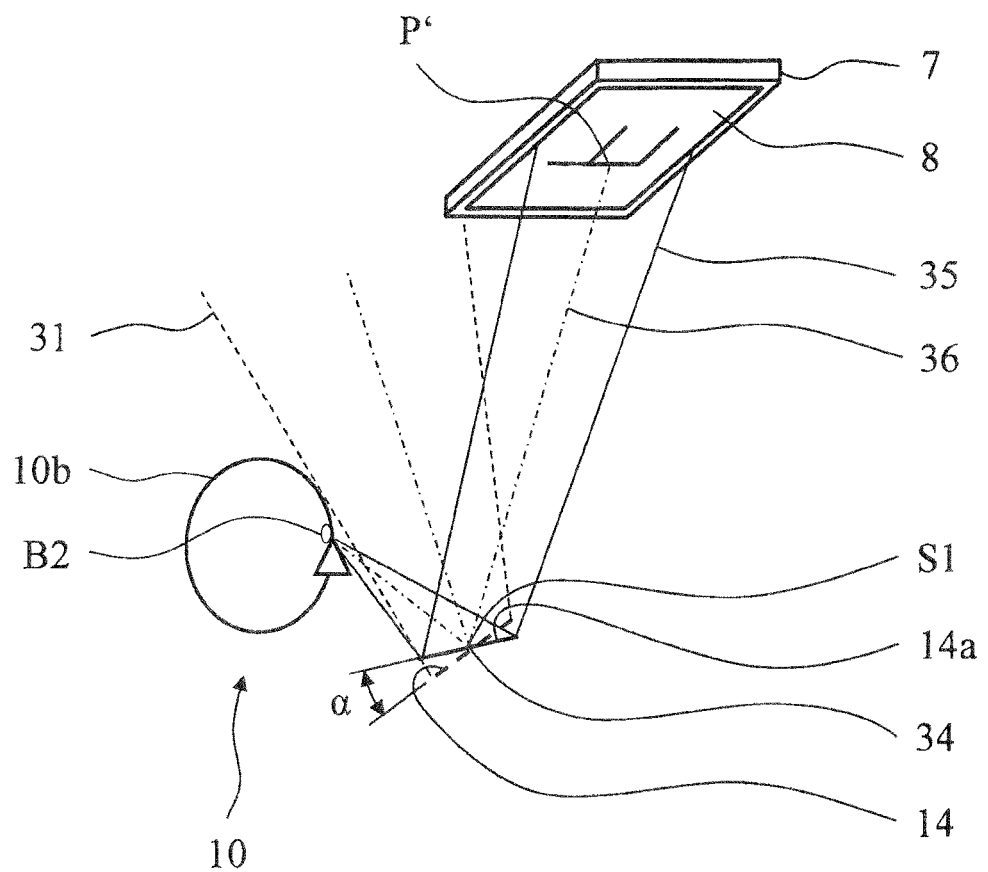
FIG. 3 shows a first embodiment for a correction of the observation situation from FIG. 2 in a side view.

FIG. 3 shows a first embodiment for a correction of the observation situation from FIG. 2 in a side view. The first mirror surface 14 is mounted horizontally rotatably. A horizontal rotation axis 34 is arranged below the mirror surface in the region of the center of the first mirror surface 14, in spatial proximity to a center point S1. The first mirror surface 14 is rotated by an angle $\alpha$ about the horizontal rotation axis 34 and is situated in a first angular setting 14a as a result. The first observer 10 in the second position 10b can see the image representation surface 8 completely again as a result. A center ray 36 passing in the center of the principal rays 35 passes from the image point P' via the center point S1 to the point B2 in the eye of the first observer 10 in the second position 10b. It should be noted at this juncture that in practice the observation situation is corrected in such a way that an optimum observation of the image representation surface is possible for both eyes of the first observer 10. For this purpose, by way of example, the point B2 can be slightly displaced and assumed to be between the pupils of the two eyes. In the case of this displacement, the accommodation of the eyes remains in the predefined range.

Figure 4:
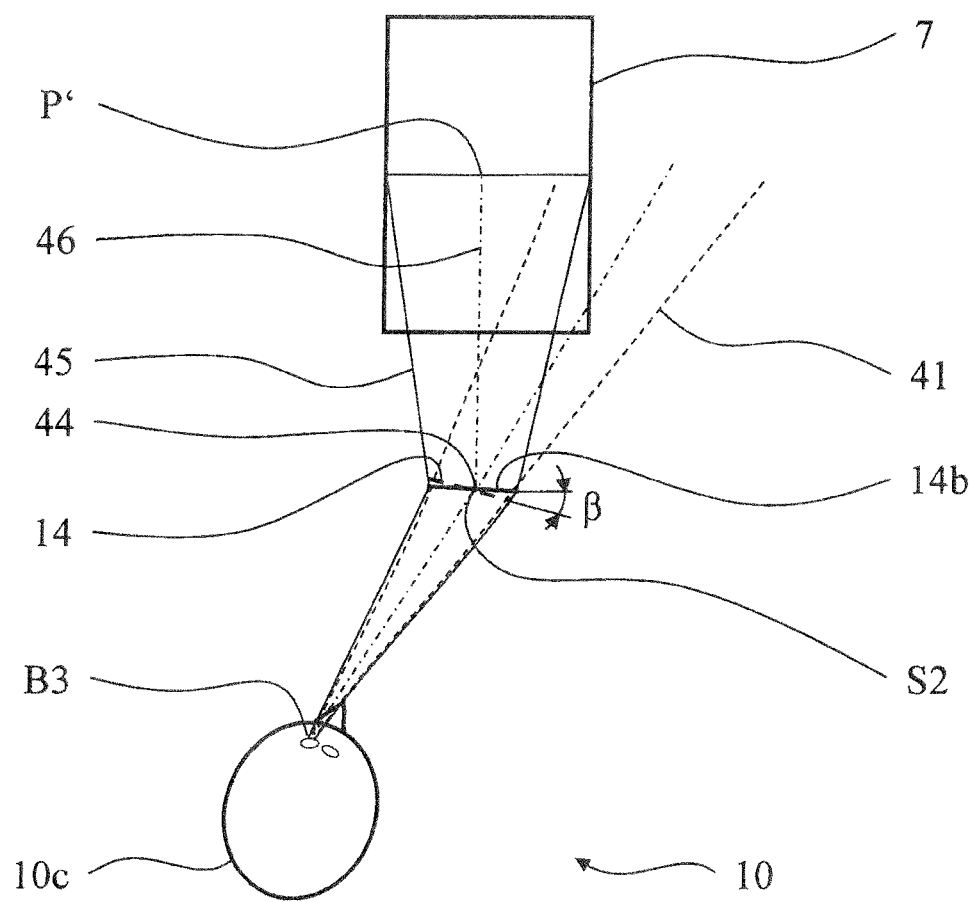
FIG. 4 shows a second embodiment for a correction of the observation situation in a view from above.

FIG. 4 shows a second embodiment for a correction of the observation situation in a view from above. The first observer 10 is situated in a third position 10c. The principal rays 41 pass from a point B3 in an eye of the first observer 10 via the first mirror surface 14 in the direction of the image representation unit 7. The first observer 10 can view only a small part of the image of the image representation unit 7 via the first mirror surface 14.

The first mirror surface 14 is mounted about a vertical rotation axis 44. The vertical rotation axis 44 is arranged in the center of the first mirror surface 14. The first mirror surface 14 is rotated by an angle $\beta$ about the vertical rotation axis 44 and is situated in a second angular setting 14b as a result. The first observer 10 in the third position 10c can see the image representation unit 7 completely again as a result. A center ray 46 passing in the center of the principal rays 45 passes from the image point P' via a center point S2 to the point B3 in the eye of the first observer 10.

The horizontal or the vertical angular setting of the first mirror surface 14 can be changed manually in a continuously variable manner or in predefined latching positions by the first observer 10. A motorized angular setting of the first mirror surface 14 is likewise conceivable. In the case of a vertical or lateral change in position of the first observer 10, the angular setting of the first mirror surface 14 can thereby be corrected in such a way that the first observer 10 can always see the center of the image representation unit 7 in the center of the first mirror surface 14.

It is also conceivable for the horizontal rotation axis 34 and the vertical rotation axis 44 to be replaced by a clampable ball-and-socket joint. The first mirror surface 14 can be set in both axial directions via a single alignment process. An angular setting of the mirror surface 14 is not limited to a horizontal rotation axis 34 or vertical rotation axis 44. It is also conceivable to be able to perform an angular setting in one or a plurality of arbitrarily oriented axial directions.

In the case of a change in position of the two observers (10, 11), a change in the distance $d_2$, or the accommodation distance, can also arise even in the case of the above-described correction of the mirror orientation. In this case, the following explanations apply equally both to the distance $d_2$ and the distance $d_4$. If the distance $d_2$ is too small, it has the consequence that the first mirror surface 14 images only part of the image of the image representation surface 8. This results in shading, since the full image representation surface 8 is not visible.

It is likewise possible for the mirror surface 14 to be displaced parallel to a focal plane in order to be able to view the image representation unit 7 completely in the first mirror surface 14. The displacement can be performed manually or by actuators.

Figure 5:
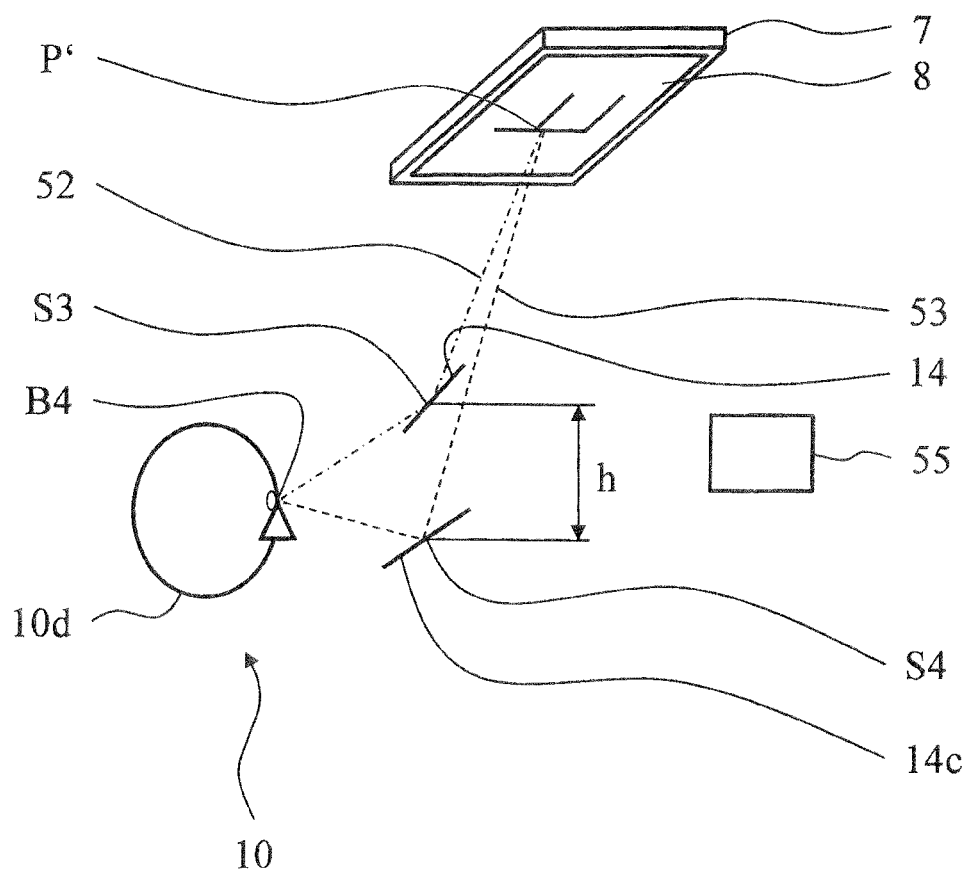
FIG. 5 shows a third embodiment for a correction of the observation situation in a side view.

FIG. 5 shows a third embodiment for a correction of the observation situation in a side view. The first observer 10, who is situated at the position 10d, can view the image of the image representation surface 8 via the first mirror surface 14. A center ray 52 passes from the image point P' on the image representation surface 8 via a center point S3 to a point B4 in the eye of the first observer 10. The distance $d_2$ of the center ray 52 is too small in this example. In addition, the first observer 10 is situated in an ergonomically unfavorable position since the observer has to direct his/her gaze obliquely upward in order to be able to see the image of the image representation surface 8 on the first mirror surface 14. In order to simplify the illustration, the marginal rays of the observation beam paths are not illustrated.

In the case of a vertical displacement of the first mirror surface 14 by a height (h) and a change in the inclination angle, the latter is situated in a position 14c. The first observer 10 can view the image of the image representation surface 8 in the first mirror surface 14 at the position 14c, with an ergonomically favorable view inclined downward by approximately 15°, relative to the horizontal. A center ray 53 passes from the image point P' on the image representation surface 8 via a center point S4 to the point B4 in the eye of the first observer 10.

The vertical displacement of the first mirror surface 14 makes it possible to correct the distance $d_2$ of a center ray from the image point P' to the eye of a first observer 10 and to set an ergonomically expedient observation position for the first observer 10.

A change in the height (h) can be performed in a continuously variable manner or in predefined latching positions. The height setting can be carried out manually by the first observer 10 or by a motorized drive.

All explanations mentioned above or below in respect of the first observer 10 are also applicable to the second observer 11. The setting possibilities described above or below in respect of the first mirror surface 14 likewise apply to the second mirror surface 15.

The setting possibilities in accordance with FIGS. 3, 4 and 5 can also be combined. An individual adaptation to different body sizes of the first observer 10 and of the second observer 11 is possible by means of a suitable mounting of the first mirror surface 14 and/or of the second mirror surface 15, the mounting being height-adjustable or variable in terms of the tilting angle.

In the simplest embodiment, the first mirror surface 14 is arranged in a stationary fashion. A motorized setting of the horizontal and vertical angles or of the height of the first mirror surface 14 is proposed in the embodiments mentioned above. A motorized setting can be carried out by step motors or servo motors. A detection of the position of the first mirror surface 14 is possible via sensors, typically encoders or potentiometers. The adaptation of the mirror position (14a, 14b, 14c) can be carried out in an automated manner if the position of the head or the eyes of the first observer 10 is determined in real time.

One simple possibility for determining the head position is to use an optical position detection system 55, also referred to as a tracking system. For this purpose, markers are attached to the head of the first observer 10, for example, to spectacles, to the first mirror surface 14 and possibly to the image representation unit 7, which are detected optically or electronically by the tracking system. The tracking system includes a tracker as measuring unit and is suitable for determining the position of all components provided with marks in space and hence the relative position of these components with respect to one another with the aid of a computation unit.

A prerequisite is that the tracker can also detect all the markers and thus the position of the components, that is, that all the components are arranged in the field of view of the tracker, without shadings by objects situated between tracker and marker. The detection of one of the components mentioned above can also be obviated if the tracker is mounted in a stationary fashion with respect thereto, for example if the tracker is arranged on the first mirror surface 14 or on the image representation unit 7.

The determination of the position of the image representation unit 7 can be obviated if the image representation unit 7 is arranged in a stationary fashion and the position thereof is determined by a calibration process when setting up the visualization apparatus 1. If the image representation unit 7 has an adjustable suspension device, however, a determination of the position of the image representation unit 7 may be necessary.

If the equipment in the operating room already includes a tracking system, it is possible, by markers being attached to the first observer 10, to the first mirror surface 14 and to the image representation unit 7, for the positions of the markers additionally to be detected. Consequently, an existing tracking system can be used to control the angular setting and/or the distance of the first mirror surface 14 with respect to the focal plane 2.

One variant of the above-described tracking system, which is suitable particularly if additional markers on the first observer 10 are disadvantageous, is to use an eye tracking system. An eye tracking system is a system or instrument for recording and analyzing viewing directions and gaze movements. The viewing data are analyzed via image processing software. The position of the head of the first observer 10 can be determined via an eye tracking system. In addition, the eye tracking system can determine the viewing direction of the first observer and thus also detect whether the first observer 10 is actually looking at the first mirror surface 14. Unnecessary setting movements of the first mirror surface 14 can thus advantageously be avoided, for example if the first observer 10 does not direct his/her gaze at the first mirror surface 14.

The eye tracking system can be arranged on the image representation unit 7 and can track the eyes and eye movements of the first observer 10 via the first mirror surface 14. It is also conceivable for the eye tracking system or the sensor of the eye tracking system to be arranged in proximity to the first mirror surface 14. It is also conceivable for the sensor of the eye tracking system to be arranged directly on the first mirror surface 14.

The position of the first mirror surface 14 can be determined by encoders or potentiometers on the joints of the mirror unit and/or a stand device to which the mirror unit is fixed. The information of the encoders or potentiometers can additionally be evaluated by the tracking or eye tracking system in order to enable a fast and very precise position setting of the first mirror surface 14.

Figure 6:
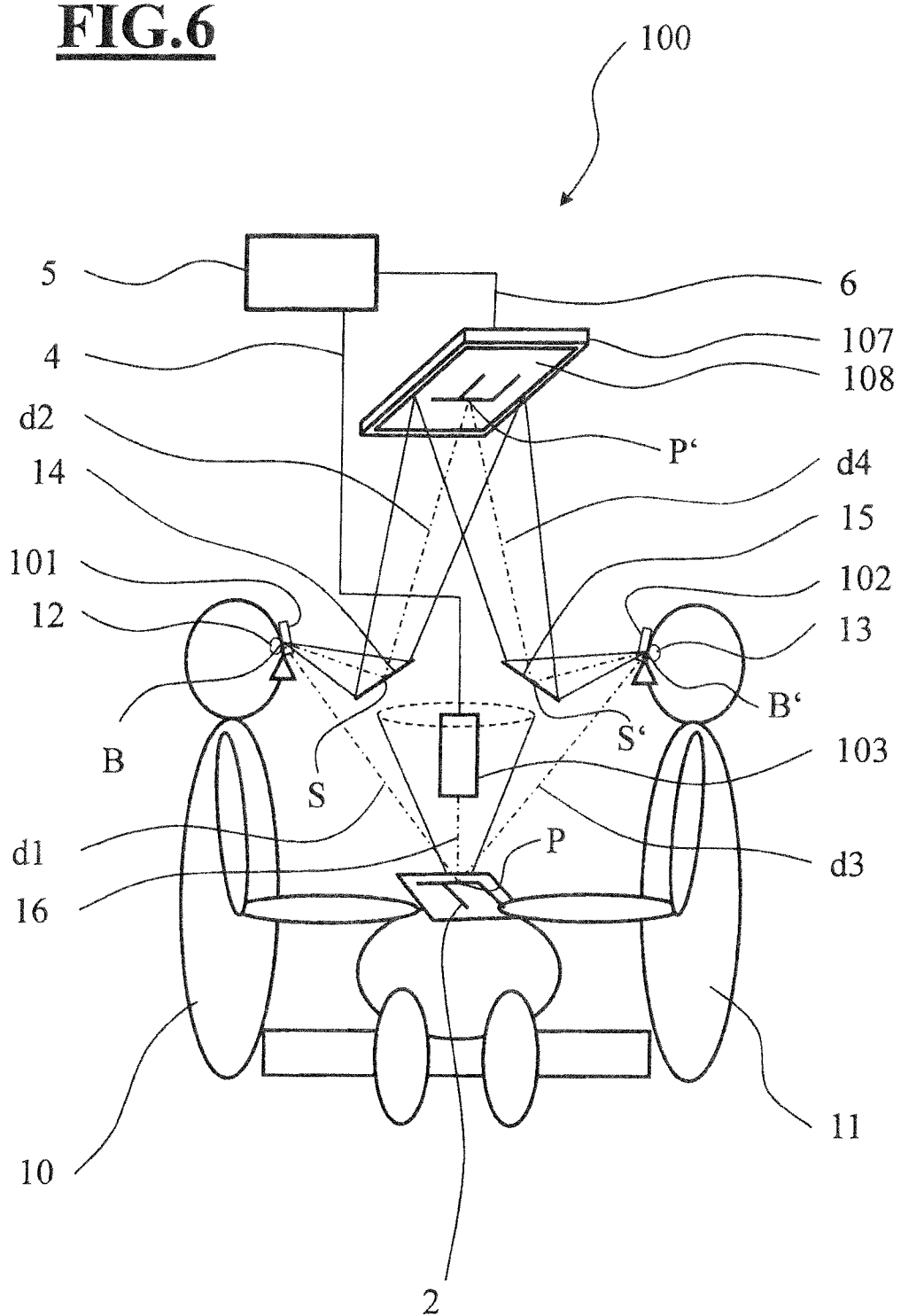
FIG. 6 is a schematic of a surgical site with a fourth embodiment of a visualization apparatus according to the invention.

FIG. 6 shows a schematic illustration of a surgical site with a fourth embodiment of a visualization apparatus 100 according to the invention.

The visualization apparatus 100 is configured like the visualization apparatus 1 in accordance with FIG. 1 and can have the same features already described in FIGS. 2 to 5, but with the difference that the visualization apparatus 100 is of stereoscopic configuration.

For this purpose, an image recording unit 103 is configured as a stereo camera and an image representation unit 107 is suitable for displaying stereoscopic partial images, perceived by the observer as a 3D image, on the stereoscopic image representation surface 108. The separation of the partial images into a right image channel for a right eye and a left image channel for a left eye is carried out via circularly polarized light. When stereoscopic partial images are displayed, for this purpose the first observer 10 has to wear first polarization spectacles 101, and the second observer 11 second polarization spectacles 102.

In this case, the first polarization spectacles 101 and the second polarization spectacles 102 are embodied differently since the two observers (10, 11) view the surgical site from opposite positions, such that a depth-correct 3D image can be perceived by both observers (10, 11).

Figure 7:
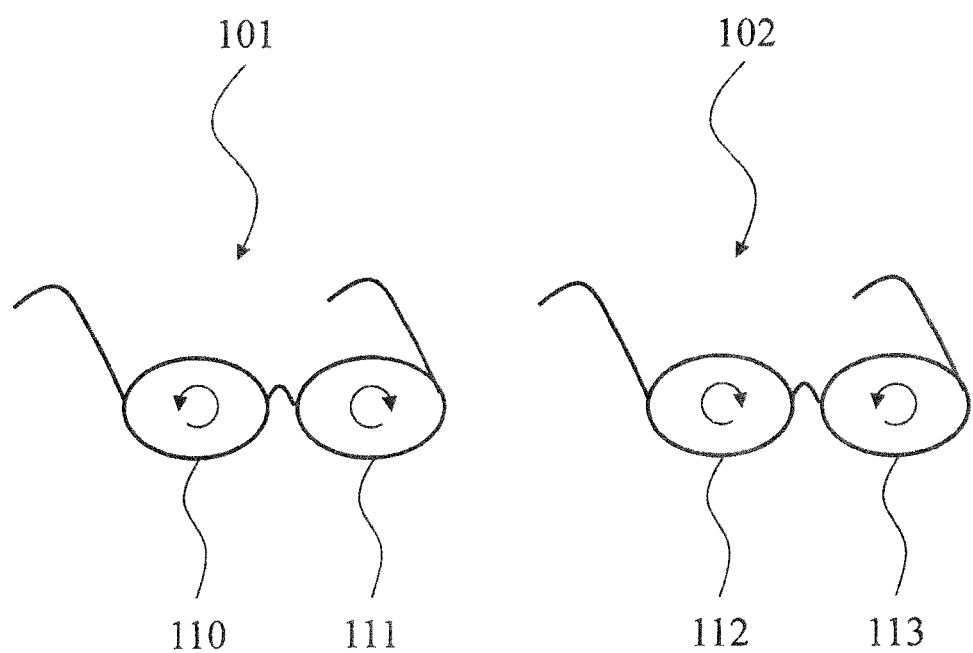
FIG. 7 is a schematic of the polarization spectacles in accordance with FIG. 6.

FIG. 7 shows a schematic illustration of the polarization spectacles in accordance with FIG. 6. The first polarization spectacles 101 are configured in such a way that they have a left-polarizing filter 110 for the right eye and a right-polarizing filter 111 for the left eye. In this case, the right-polarizing filter 111 is constructed such that it transmits substantially only right-circularly polarized light, while left-circularly polarized light is almost not transmitted. The left-polarizing filter 110 transmits substantially only left-circularly polarized light, while right-circularly polarized light is almost not transmitted. Circularly polarizing filters (110, 111) can be constructed, for example, by the combination of a $\lambda/4$ plate with a linearly polarizing filter that transmits only light having a linear polarization direction. The second polarization spectacles 102 for the second observer 11 are constructed exactly oppositely and have a right-polarizing filter 112 for the right eye and a left-polarizing filter 113 for the left eye. This embodiment has the disadvantage that the first observer 10 and the second observer 11 have to change or swap the polarization spectacles in the event of changing to an opposite observation position.

In order, with the same polarization spectacles, to be able to view the surgical site from both observation situations and to view the surgical site as a depth-correct 3D image, it is proposed to introduce a $\lambda/2$ retardation plate into one of the two beam paths.

Figure 8:
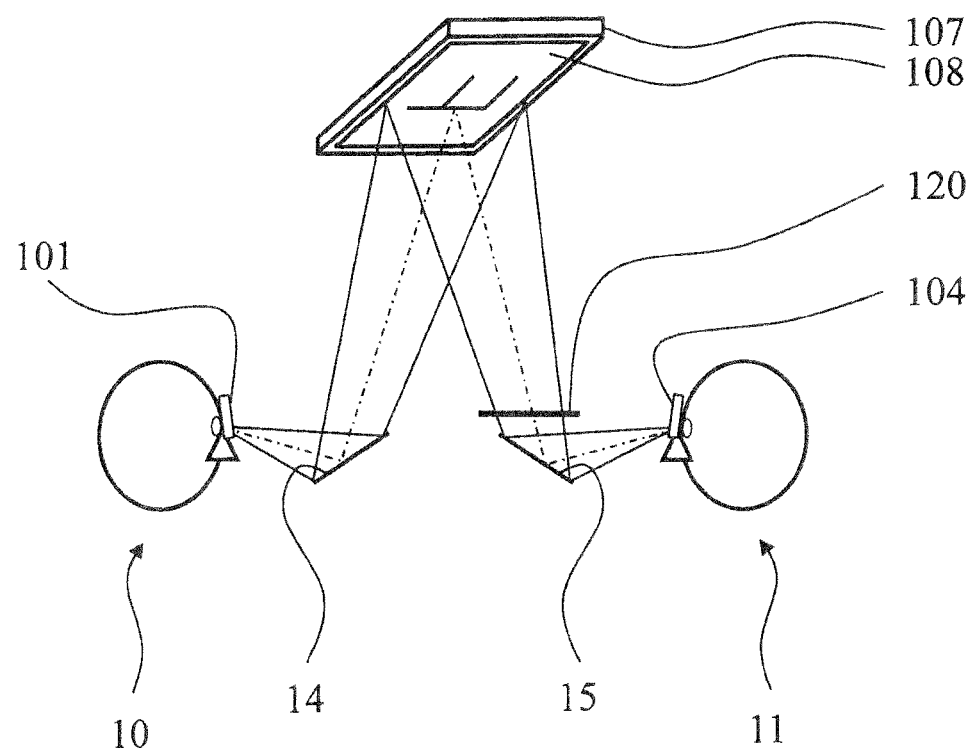
FIG. 8 shows a fifth embodiment of an observation situation in a schematic illustration.

FIG. 8 shows a fifth embodiment of such an observation situation in a schematic illustration. The visualization apparatus in accordance with FIG. 8 has the same features as in FIG. 6, but with the difference that for the second observer 11 a $\lambda/2$ retardation plate 120 is introduced into the beam path above the second mirror surface 15. The $\lambda/2$ retardation plate has the effect that the polarization direction for the left and right stereoscopic partial beams is reversed in each case. Consequently, the second observer 11 can wear polarization spectacles 104 identical to the first polarization spectacles 101 of the first observer 10, and view a depth-correct 3D image of the operation site. In the event of a change in the two observation positions, both observers (10, 11) can keep their polarization spectacles (101, 104).

This has the further advantage that it is merely necessary to provide a single type of polarization spectacles (101, 104). This saves space and storage costs; moreover, the situation in which the observers (10, 11) mistakenly put on incorrect polarization spectacles is precluded.

Alternatively, it is also conceivable to introduce the $\lambda/2$ retardation plate 120 into the beam path between the mirror surface 15 and second observer 11. The solution shown in FIG. 8 is preferred, however, for space reasons.

Likewise, it is alternatively possible to introduce the $\lambda/2$ retardation plate 120 into the beam path for the first observer 10, preferably above the first mirror surface 14. In this case, however, both observers (10, 11) would have to wear second polarization spectacles 102.

In order to clarify the effect of the $\lambda/2$ retardation plate, it is assumed that the first polarization spectacles 101 have for the right eye a left-polarizing filter 110 having a polarization axis at an angle of +45° and for the left eye a right-polarizing filter 111 having a polarization axis at an angle of −45°. Without a $\lambda/2$ retardation plate, a transmission value of 3.6% for the left eye and a transmission value of 90.1% for the right eye result for the left image channel. These values are interchanged when a $\lambda/2$ retardation plate is introduced into the beam path. The left image channel then has a transmission value of 90.1% for the left eye and 3.6% for the right eye.

In this embodiment, the $\lambda/2$ retardation plate 120 is embodied as a plane-parallel plate having a thickness of 0.161813 mm. Plane-parallel plates having a thickness of 0.1618 mm are also encompassed within the scope of the invention. Moreover, the thicknesses of a plane-parallel plate for which substantially the same physical effect occurs are also intended to be concomitantly encompassed. Quartz having a crystal axis along a first axis of the crystal structure is assumed as the medium of the retardation layer, wherein the first axis of the crystal structure is oriented parallel to the surface of the plane-parallel $\lambda/2$ retardation plate 120. If the beam impinges on the first interface of the $\lambda/2$ retardation plate 120 perpendicularly from the image representation surface 108, a transmission value of 81.9% for the left eye and a transmission value of 3.3% for the right eye hold true for the left image channel. The retardation layer thus converts left-circularly polarized light into right-circularly polarized light. The conversion takes place as a result of the retarding effect of the retardation elements, or as a result of the anisotropic effect of the uniaxial quartz crystals. Only the retarding effect is considered for the retardation elements, since the effect of a rotational birefringence is of secondary importance in this embodiment.

Figure 9:
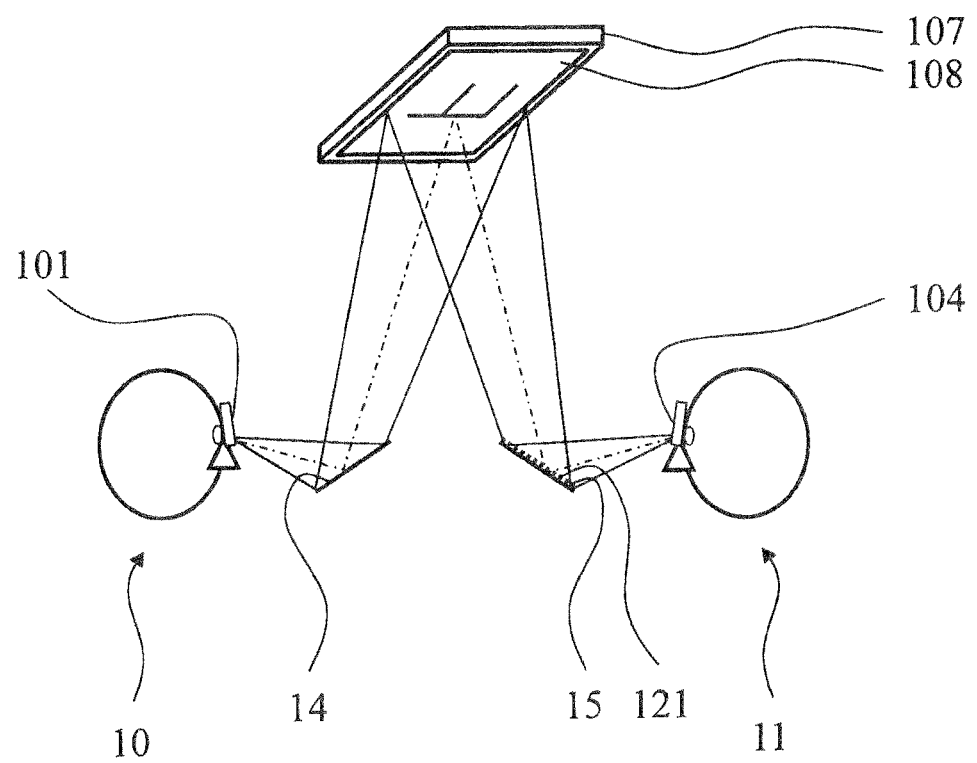
FIG. 9 shows a sixth embodiment of an observation situation in a schematic illustration.

FIG. 9 shows a sixth embodiment of an observation situation in a schematic illustration. This embodiment differs from the embodiment in accordance with FIG. 8 in that the $\lambda/2$ retardation plate 120 is replaced by a $\lambda/4$ retardation layer 121 applied on the second mirror surface 15.

In order to clarify the effect of the $\lambda/4$ retardation layer 121, it is assumed that the first polarization spectacles 101 have for the right eye a left-polarizing filter 110 having a polarization axis at an angle of +45° and for the left eye a right-polarizing filter 111 having a polarization axis at an angle of −45°. Without a $\lambda/4$ retardation layer, a transmission value of 3.6% for the left eye and a transmission value of 90.1% for the right eye result for the left partial beam path. When a $\lambda/4$ retardation layer is introduced into the beam path, wherein the $\lambda/4$ retardation layer is fitted directly on the second mirror surface 15, these values are interchanged. In the case of an ideal $\lambda/4$ retardation layer, the left image channel has a transmission value of 90.1% for the left eye and a transmission value of 3.6% for the right eye. In the case of an anisotropic $\lambda/4$ retardation layer 121 in the form of a 0.071926 mm thick plane-parallel plate composed of quartz that is arranged directly on the mirror surface 15, the desired polarization reversal is obtained. Plane-parallel plates having a thickness of 0.0719 mm are also encompassed within the scope of the invention. Moreover, the thicknesses of a plane-parallel plate for which substantially the same physical effect occurs are also intended to be concomitantly encompassed. In this case, the crystal axis of the plane-parallel plate is oriented along a first axis of the crystal structure, parallel to the surface of the plane-parallel plate. The left image channel has a transmission value of 75.9% for the left eye and a transmission value of 1.1% for the right eye. However, if the crystal axis of the quartz is arranged along a second axis oriented orthogonally to the first axis of the crystal structure and parallel to the surface of the retardation layer, the desired polarization reversal is not obtained.

A light beam emitted individually by the image representation surface 108 at a wavelength $\lambda=589$ nm was assumed by way of example for the calculation of the transmission values mentioned above. The calculation was made under the assumption of a circular start polarization and a mirror surface 15 arranged at 45° relative to the start beam direction, such that a second observer 11 can view the light beam at 90° through the polarization spectacles 104. A retardation element composed of quartz having a main refractive index of $n_o=1.5442$ and $n_e=1.5533$ at $\lambda=589$ nm was chosen as material parameters. A mirror including silver (solid) as substrate material having a refractive index of n=0.20 and an absorption coefficient nk=3.44 at $\lambda=589.3$ nm was assumed for the mirror surface 15. Since the refractive index is relative to a metal, it can be less than 1. The absorption coefficient nk is dimensionless and describes the product of refractive index n and absorption index k ("kappa").

If the $\lambda/4$ retardation layer 121 is combined with the reflection layers of the second mirror surface 15, then the reflectance and its dependence on the wavelength and the direction of the incident beam can be optimized further for this "retardation mirror". For this purpose, the $\lambda/4$ retardation layer 121 can be composed of a plurality of individual layers which overall form a $\lambda/4$ retardation layer. These individual layers can in turn be integrated into the layer stack that forms the reflection partial layers of the second mirror surface 15. Likewise, it is alternatively also possible to introduce the $\lambda/4$ retardation layer 121 directly on the first mirror surface 14 into the beam path for the first observer 10. In this case, however, both observers (10, 11) would have to wear second polarization spectacles 102.

Figure 10:
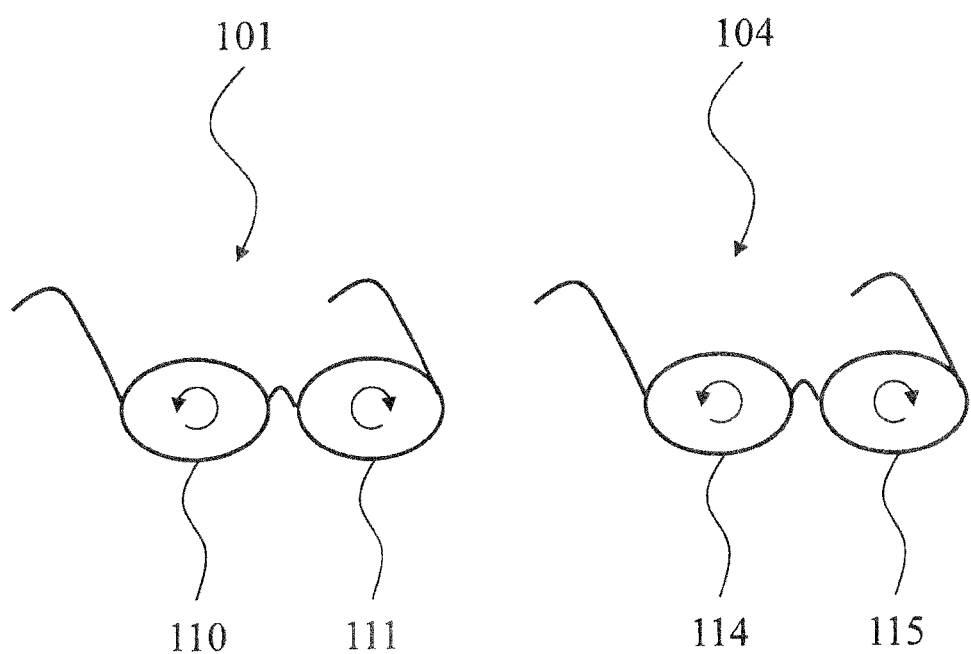
FIG. 10 is a schematic of the polarization spectacles in accordance with FIG. 8 and FIG. 9; and, FIG. 11 shows a seventh embodiment in a schematic illustration.

FIG. 10 shows a schematic illustration of the polarization spectacles in accordance with FIG. 8 and FIG. 9. The third polarization spectacles 104 are embodied identically to the first polarization spectacles 101 and have for the right eye a left-polarizing filter 114 and for the left eye a right-polarizing filter 115. FIG. 10 shows that, in the embodiments in accordance with FIGS. 8 and 9, the first observer 10 and the second observer 11 in opposite observation positions wear the same polarization spectacles (101, 104).

Figure 11:
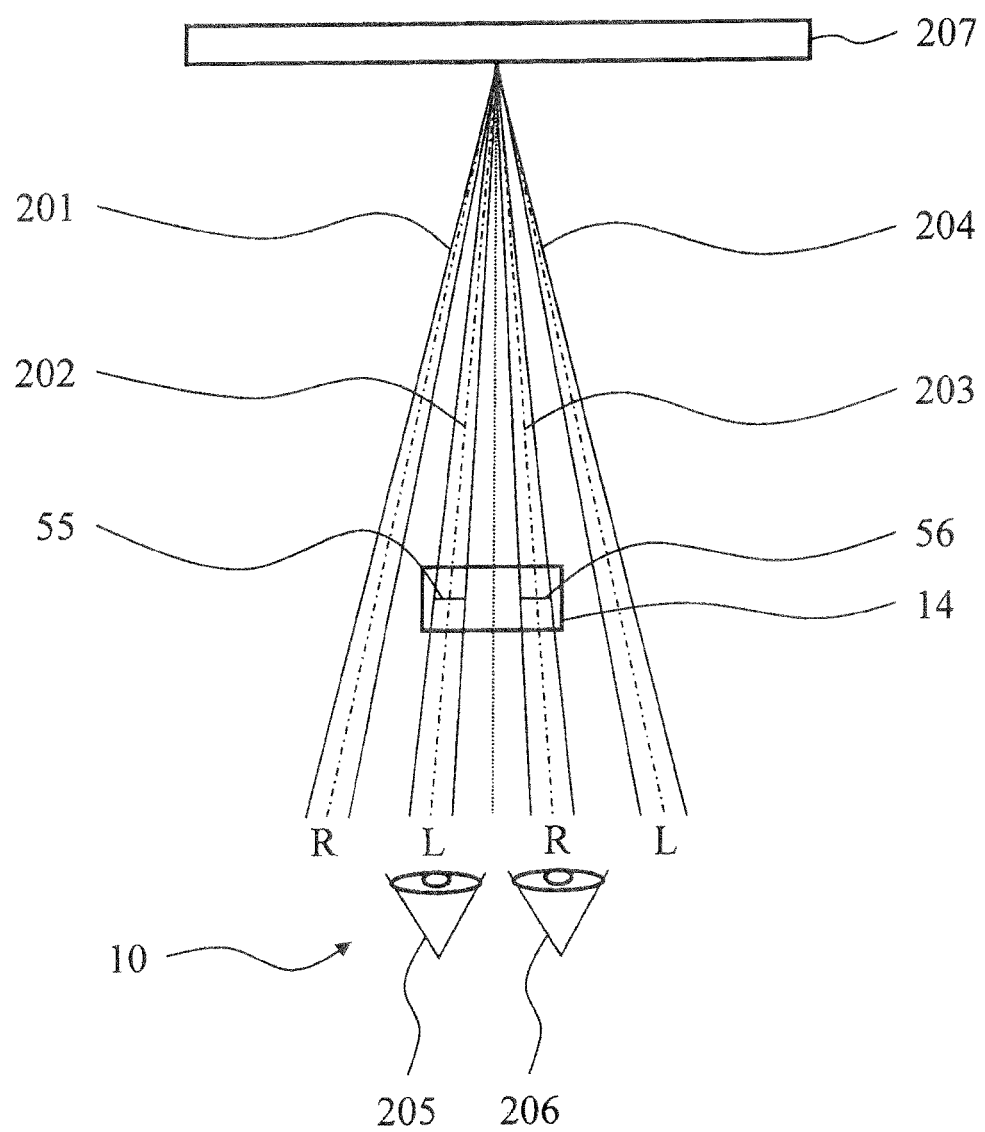

FIG. 11 shows a seventh embodiment in a schematic illustration. The figure illustrates the observation situation only for a first observer 10. With the use of a stereoscopic camera as image recording unit 103 in accordance with FIG. 6, in the case of an arrangement of the image representation unit and the first mirror surface 14 in accordance with FIG. 6, it is possible to use an autostereoscopic 3D monitor 207 as image representation unit. The stereoscopic camera has a left channel and a right channel. The autostereoscopic 3D monitor 207 emits beams of the left channel or of the right channel in specific preferred directions. A first beam 201 is assigned to the right channel R, a second beam 202 is assigned to the left channel L, a subsequent third beam 203 is in turn assigned to the right channel R and a fourth beam 204 to the left channel L, et cetera. The first mirror surface 14 is arranged in such a way that it reflects exactly two beams, in the example the second beam 202 with the left channel L and the third beam 203 with the right channel R at the mirror surface 14. A first observer 10 can observe the second beam 202 with a left eye 205 and the third beam 203 with a right eye 206. Since the first mirror surface 14 reflects exactly two beams (202, 203) in an isolated manner for the first observer 10, no interchange of right and left and thus also no depth reversal can take place.

For the second observer 11, who is situated on the opposite side of the operation site in accordance with FIG. 6, the applicable conditions are exactly the opposite. In order to be able to view the operation site laterally correctly via the second mirror surface 15, the second mirror surface 15 reflects a right beam R for the left eye of the second observer 11 and a left beam L for the right eye. The respective left and right eyes of the two observers (10, 11) thus advantageously receive, without further aids and without polarization spectacles, the laterally correct image intended for them delivered with correct depth relation. Both observers (10, 11) can view the operation site both directly and via the mirror surface (14, 15) without additional polarization spectacles.

So-called light field displays are also suitable as stereoscopic image representation unit, in which displays a light field that includes the three-dimensional image information is generated with the aid of a microlens array. Such light field displays have the advantage that the 3D image can be viewed without the use of polarization spectacles.

It is understood that the foregoing description is that of the preferred embodiments of the invention and that various changes and modifications may be made thereto without departing from the spirit and scope of the invention as defined in the appended claims.

| LIST OF REFERENCE SIGNS | |
|---|---|
| 1 | visualization apparatus |
| 2 | focal plane |
| 3 | image recording unit |
| 4 | first line |
| 5 | control unit |
| 6 | second line |
| 7 | image representation unit |
| 8 | image representation surface |
| 10 | first observer |
| 10a | first position of the first observer |
| 10b | second position of the first observer |
| 10c | third position of the first observer |
| 10d | fourth position of the first observer |
| 11 | second observer |
| 12 | first eye of the first observer |
| 13 | second eye of the second observer |
| 14 | first mirror surface |
| 14a | first angular setting |
| 14b | second angular setting |
| 14c | position |
| 15 | second mirror surface |
| 16 | optical axis |
| 30 | principal rays |
| 31 | principal rays |
| 34 | horizontal rotation axis |
| 35 | principal rays |
| 36 | center ray |
| 41 | principal rays |
| 44 | vertical rotation axis |
| 45 | principal rays |
| 46 | center ray |
| 52 | center ray |
| 53 | center ray |
| 55 | position detection system |
| 100 | visualization apparatus, stereoscopic |
| 101 | first polarization spectacles |
| 102 | second polarization spectacles |
| 103 | image recording unit, stereoscopic |
| 104 | third polarization spectacles |
| 107 | image representation unit, stereoscopic |
| 108 | image representation surface, stereoscopic |
| 110 | left-polarizing filter |
| 111 | right-polarizing filter |
| 112 | right-polarizing filter |
| 113 | left-polarizing filter |
| 114 | left-polarizing filter |
| 115 | right-polarizing filter |

-continued

LIST OF REFERENCE SIGNS

| 120 | λ/2 retardation plate |
| 121 | λ/4 retardation layer |
| 201 | first beam |
| 202 | second beam |
| 203 | third beam |
| 204 | fourth beam |
| 205 | left eye |
| 206 | right eye |
| 207 | autostereoscopic 3D monitor |

What is claimed is:

1. A visualization apparatus for a surgical site, comprising:
an image recording unit defining a focal plane and being configured to record an image of an object arranged in said focal plane of said image recording unit;
said image recording unit including a lens having an optical axis that intersects said focal plane at a point P;
an electronic image representation unit having an image representation surface for reproducing the image recorded by said image recording unit, wherein said point P is reproduced at an image point P' of said image representation surface of said image representation unit;
a first mirror unit having a first mirror surface arranged relative to said image representation surface in such a manner that the image reproduced by said image representation surface is reflected by said first mirror surface;
said first mirror surface having a first center point S; and,
said focal plane, said image representation surface and said first mirror surface being arranged relative to one another in such a manner that a first observation point B results for which the following applies:

$-2\ D < \Phi 1 - \Phi 2 < +2\ D$;

wherein:
$\Phi 1 = -1/d_1$
$\Phi 2 = -1/d_2$
$d_1$=distance $\overline{PB}$
$d_2$=distance $\overline{P'S}$+distance $\overline{SB}$.

2. The visualization apparatus of claim 1, wherein the following applies:

$-1\ D < \Phi 1 - \Phi 2 < +1\ D$.

3. The visualization apparatus of claim 1, wherein the following applies:

$-0.5\ D < \Phi 1 - \Phi 2 < +0.5\ D$.

4. The visualization apparatus of claim 1, wherein said first mirror unit has at least one of a first device configured to rotate said first mirror surface about at least one axis, a second device configured to change a distance between said first mirror surface and said focal plane and a third device configured to displace said first mirror surface parallel to said focal plane.

5. The visualization apparatus of claim 1 further comprising:
a second mirror unit having a second mirror surface; said second mirror surface having a second center point S' and being arranged relative to said image representation surface in such a way that the image reproduced by said image representation surface is reflected by said second mirror surface;
said focal plane, said image representation surface and said second mirror surface being arranged relative to one another in such a way that a second observation point B' results for which the following applies:

$-2\ D < \Phi 3 - \Phi 4 < +2\ D$ wherein:
$\Phi 3 = -1/d_3$
$\Phi 4 = -1/d_4$
$d_3$=distance $\overline{PB'}$
$d_4$=distance $\overline{P'S'}$+distance $\overline{S'B'}$.

6. The visualization apparatus of claim 5, wherein the following applies:

$-1\ D < \Phi 3 - \Phi 4 < +1\ D$.

7. The visualization apparatus of claim 5, wherein the following applies:

$-0.5\ D < \Phi 3 - \Phi 4 < +0.5\ D$;

8. The visualization apparatus of claim 5, wherein said second mirror unit has at least one of a first device configured to rotate said second mirror surface about at least one axis, a second device configured to change a distance between said second mirror surface and said focal plane and a third device configured to displace said second mirror surface parallel to said focal plane.

9. The visualization apparatus of claim 1, wherein said image representation unit is arranged above said image recording unit.

10. The visualization apparatus of claim 9, wherein said image representation surface is aligned at an angle of a maximum of 15° parallel to the focal plane; and, said image representation surface has an emission direction directed to said focal plane.

11. The visualization apparatus of claim 9, wherein said image representation surface is arranged in such a way that said image representation surface has a center point lying in the extension of said optical axis of said lens of said image recording unit.

12. The visualization apparatus of claim 9, wherein at least one of said first mirror surface and a second mirror surface of a second mirror unit are arranged between said image recording unit and said image representation surface.

13. The visualization apparatus of claim 1, wherein said image recording unit is configured to record a stereoscopic image and said image representation surface is configured to reproduce said stereoscopic image.

14. The visualization apparatus of claim 13 further comprising a λ/2 retardation plate arranged in the beam path between said image representation surface and the first mirror surface.

15. The visualization apparatus of claim 13 further comprising:
a second mirror unit having a second mirror surface; said second mirror surface having a second center point S' and being arranged relative to said image representation surface in such a way that the image reproduced by said image representation surface is reflected by said second mirror surface;
said focal plane, said image representation surface and said second mirror surface being arranged relative to one another in such a way that a second observation point B' results for which the following applies:

$-2\ D < \Phi 3 - \Phi 4 < +2\ D$ wherein:
$\Phi 3 = -1/d_3$ $\Phi_4 = -1/d_4$ $d_3$ = distance $\overline{PB'}$ $d_4$ = distance $\overline{P'S'}$ + distance $\overline{S'B'}$; and, a λ/2 retardation plate arranged in the beam path between the image representation surface and the first mirror surface or in the beam path between said image representation surface and said second mirror surface.

16. The visualization apparatus of claim 13, wherein said first mirror surface has a λ/4 retardation layer.

17. The visualization apparatus of claim 13 further comprising:

a second mirror unit having a second mirror surface; said second mirror surface having a second center point S' and being is arranged relative to said image representation surface in such a way that the image reproduced by said image representation surface is reflected by said second mirror surface;

said focal plane, said image representation surface and said second mirror surface being arranged relative to one another in such a way that a second observation point B' results for which the following applies:

−2 D<Φ3−Φ4<+2 D wherein:

$\Phi_3 = -1/d_3$ $\Phi_4 = -1/d_4$ $d_3$ = distance $\overline{PB'}$ $d_4$ = distance $\overline{P'S'}$ + distance $\overline{S'B'}$; and, said second mirror surface has a λ/4 retardation layer.

18. The visualization apparatus of claim 13, wherein said image representation unit is configured as an autostereoscopic 3D monitor.

19. The visualization apparatus of claim 1 further comprising:

at least one of a first actuator and a second actuator;

said first actuator being configured to rotate said first mirror surface about a first axis;

said first mirror surface and said focal plane conjointly defining a first distance therebetween;

said second actuator being configured to change said first distance;

a first position detection system configured to detect a position of at least one of the eyes and the head of a first observer relative to said first mirror surface;

a control unit connected to said first position detection system and to at least one of said first actuator and said second actuator;

said control unit being configured in such a way that at least one of the rotation of said first mirror surface and the change in said first distance can be set by the position of at least one of the eyes and the head of the first observer as detected by said first position detection system.

20. The visualization apparatus as claimed in claim 19 further comprising:

a second mirror unit having a second mirror surface; said second mirror surface having a second center point S' and being arranged relative to said image representation surface in such a way that the image reproduced by said image representation surface is reflected by said second mirror surface;

said focal plane, said image representation surface and said second mirror surface being arranged relative to one another in such a way that a second observation point B' results for which the following applies:

−2 D<Φ3−Φ4<+2 D wherein:

$\Phi_3 = -1/d_3$ $\Phi_4 = -1/d_4$ $d_3$ = distance $\overline{PB'}$ $d_4$ = distance $\overline{P'S'}$ + distance $\overline{S'B'}$;

at least one of a third actuator and a fourth actuator;

said third actuator being configured to rotate said second mirror surface about a second axis;

said second mirror surface and said focal plane conjointly defining a second distance between each other;

said fourth actuator being configured to change said second distance;

a second position detection system configured to detect a position of at least one of the eyes and the head of a second observer relative to said second mirror surface;

said control unit being connected to said second position detection system and to at least one of said third actuator and said fourth actuator; and, said control unit being further configured in such a way that at least one of the rotation of said second mirror surface and the change of the distance of said second mirror surface to said focal plane can be set by the position of at least one of the eyes and the head of the second observer as detected by said second position detection system.

* * * * *